United States Patent [19]

Fisher

[11] 3,931,305

[45] Jan. 6, 1976

[54] TEREPHTHALIC ACID RECOVERY BY CONTINUOUS FLASH CRYSTALLIZATION

[75] Inventor: Jay A. Fisher, Naperville, Ill.

[73] Assignee: Standard Oil Company, Chicago, Ill.

[22] Filed: Aug. 20, 1973

[21] Appl. No.: 389,717

[52] U.S. Cl. .............................. 260/525; 260/515 P
[51] Int. Cl.² .................. C07C 51/46; C07C 51/44; C07C 63/26
[58] Field of Search .................................... 260/525

[56] References Cited
UNITED STATES PATENTS

| | | | |
|---|---|---|---|
| 3,639,465 | 2/1972 | Olsen et al. ......................... | 260/525 |
| 3,708,532 | 1/1973 | Ichikawa ............................ | 260/525 |

FOREIGN PATENTS OR APPLICATIONS

| | | | |
|---|---|---|---|
| 1,261,530 | 1/1972 | United Kingdom ................. | 260/519 |

*Primary Examiner*—Lorraine A. Weinberger
*Assistant Examiner*—Richard D. Kelly
*Attorney, Agent, or Firm*—Fred R. Ahlers; Arthur G. Gilkes; William T. McClain

[57] ABSTRACT

Inordinately slow crystallization at rate controlled evaporative cooling of terephthalic acid from liquid phase aqueous solutions also containing from 500 to 6,000 ppm p-toluic acid based on dissolved terephthalic acid at temperatures in the range of 400° to 550°F. can be overcome by more rapid continuous flash evaporation of solvent in two or more stirred crystallization zones to obtain a terephthalic acid product having 150 ppm or less p-toluic acid. Such product is readily separated from mother liquor by continuous centrifuge.

8 Claims, No Drawings

TEREPHTHALIC ACID RECOVERY BY CONTINUOUS FLASH CRYSTALLIZATION

BACKGROUND OF INVENTION

Commercial crude terephthalic acid contains on a weight basis from 800 to 7,000 parts per million (ppm) 4-carboxybenzaldehyde 200 to 1,500 ppm p-toluic acid as the main impurities and some crude terephthalic acid also contain lesser amounts, 200–20 ppm range, of yellow colored aromatic compounds having the structures of benzil, fluorenone or anthraquinone which are characteristically yellow compounds as impurities resulting from coupling side reactions occurring during the oxidation of p-xylene.

U.S. Pat. No. 3,584,039 issued to Delbert H. Meyer teaches a feasible, commercially useful method for purification of such commercially available crude terephthalic acid products by treating liquid phase solutions thereof in water at temperatures of 200°–374° C. with hydrogen in the presence of a solid hydrogenation catalyst (e.g., metallic palladium on carbon support) and crystallizing terephthalic acid from catalyst-free liquid phase solutions at temperatures in the range of 50° to 150° C. The catalytic hydrogen treatment converts 4-carboxybenzaldehyde to p-toluic acid and decolorizes the terephthalic acid.

British Pat. No. 1,152,575 is directed to the development of the Meyer Patent method for its commercial application by providing improved modes of conduct for the entire process from the step of dissolving crude terephthalic acid through the step of crystallizing terephthalic acid from the hydrogen treated aqueous solution. With respect to said crystallization, said British patent teaches the use of solvent evaporation to effect the cooling necessary to precipitate crystalline terephthalic acid but cautions that conduct of such evaporative cooling should avoid shock cooling of the solution as would occur by instantaneous flash evaporation of solvent because such shock cooling coprecipitates dissolved impurities which contaminate terephthalic acid product. To prevent the contaminating effect of such shock cooling, the British patent teaches that the evaporative cooling should be controlled by evaporation against equilibrium back pressure, for example, by throttling of steam vapor exhaust at the equilibrium pressure. This is in effect a controlled rate evaporative cooling.

Crystallization by controlled rate evaporative cooling is, according to the above British patent, applied to continuous crystallization conducted in three series connected stages under the conditions described to effect in 3.4 hours a 302° F. temperature drop from 530° F. initial solution temperature to the third stage temperature of 228° F. This mode of conducting said crystallization provided an average cooling rate of 1.48° F. per minute was not only inordinately slow but, when applied to aqueous solutions of terephthalic acid of 2,400 ppm p-toluic acid content, also provided a terephthalic acid product containing 1,200 ppm p-toluic acid. Such product would not be acceptable for direct reaction with ethylene glycol for polyester fiber manufacture.

U.S. Pat. No. 3,452,088 repeats the caution against shock cooling and teaches a further improvement for the continuous controlled rate evaporative cooling technique as applied to crystallizing terephthalic acid from aqueous solutions also containing dissolved p-toluic acid. The improvement consists of limiting the final crystallization temperature and/or crystalline product separation temperature to the temperature range of 250° to 300° F. to prevent p-toluic acid contamination of crystallizing terephthalic acid. By using such final crystallization and/or product separation temperatures of 250° to 300° F. terephthalic acid could be and was commercially obtained with 150 ppm and less p-toluic acid from feed solutions containing 6,000 to 500 ppm p-toluic acid at a somewhat faster cooling rate of 3°–4° F. per minute. But such faster controlled rate evaporation process does not provide a useful basis for devising still faster continuous flash evaporative crystallization to overcome the p-toluic acid contamination problem mentioned in both the British and U.S. patents.

Crystallization by flash evaporation of solvent has, in general, been long known and used to take advantage of the substantially instantaneous decrease in both temperature and pressure and attendant substantially instantaneous evaporation of solvent as the hot solution of solute is introduced into the crystallization vessel operated at a lower temperature and pressure. Advantageously, the rapidly vaporized portion of the liquid solvent flashed to the vapor phase permits rapid removal of solvent vapor. Both crystallization and crystal growth occur rapidly with the cooling and concentrating caused by flashing the solution to the lower temperature. Growth of crystals is substantially entirely the lower temperature and is independent of residence time. Crystal size in a crystallization vessel where solvent is flash evaporated can, as is well known, be enhanced by circulation of slurry of crystals throughout the lower portion of the crystallization vessel. For example, one means for accomplishing such circulation in a stirred crystallization zone is to withdraw a portion of the slurry from near its upper level and introduce, e.g., by pumping, the withdrawn slurry up through the bottom of the stirred slurry.

However, use of flash solvent evaporation induced crystallization of terephthalic acid (TA) from aqueous solution also containing dissolved p-toluic acid in amounts of 500 to 6,000 ppm based on TA can, without proper conduct thereof, bring into play the p-toluic acid contamination phenomenon alluded to in the British patent and more generally described in the later U.S. patent. Such contamination phenomenon is somewhat anomalous because, in spite of the fact that there is retained more than enough solvent water to prevent saturation or supersaturation with respect to p-toluic acid, p-toluic acid nevertheless comes out of solution. Said later U.S. patent suggests that the contamination phenomenon is in some way dependent on the rate of crystallization and the final temperature of crystallization and product separation and not solely on p-toluic acid concentration in the solution.

From plots of TA saturation and supersaturation (TA concentrations vs. temperature) and the guidance provided by teachings in the aforementioned related British and United States patents, one might devise a continuous TA crystallization process having a number of crystallization stages in series with each stage operated at a temperature lower than the preceding stage and, for smooth operation approximating batchwise crystallization, having a temperature profile substantially following the TA saturation plot. Such a devised continuous crystallization process would have at least about 40 rate dependent crystallization stages. However, because of the number of stages and their time consuming operation, such a continuous crystallization would not be economically attractive or feasible for commercial application.

SUMMARY OF INVENTION

A process of producing terephthalic acid having 150 ppm or less p-toluic acid content by weight (i.e., fiber-grade quality TA) has been discovered which is applicable to aqueous solutions of TA having 500–6,000 ppm by weight of p-toluic acid and advantageously makes use of substantially instantaneous crystallization of incremental proportions of dissolved TA in a small number, at least two, series connected stirred crystallization zones. Such continuous crystallization can be successfully applied to aqueous solutions substantially saturated with TA at temperatures in the range of 400° to 500° F., provided that at least the zones operated at temperatures of 360°–320° F. and below, and preferably all the zones are so operated to crystallize decreasing proportions of originally dissolved TA. The success of the present inventive process, as will hereinafter be demonstrated, is indeed surprising in view of the aforementioned prior teaching that flash evaporation of solvent to effect TA crystallization from aqueous solution also containing dissolved p-toluic acid will only lead to TA excessively contaminated with p-toluic acid.

The choice of the real and effective number of series connected stirred crystallization zones using flash evaporation of water is associated with the concentration of p-toluic acid based on TA and not on the p-toluic acid concentration in the solution fed to any one zone and, since crystallization of each incremental amount of TA is substantially instantaneous, not on any rate dependent technique for effecting TA crystallization. For such initially dissolved TA having 500–6,000 ppm of p-toluic acid by weight based on TA, the number of such flash evaporations of solvent in series, in general, will not exceed a total of eight stirred crystallization zones. For example, two such zones are adequate for 500–1,000 ppm p-toluic acid, three such zones are adequate for 500–3,000 ppm p-toluic acid, four such zones are adequate for 1,500–4,000 ppm p-toluic acid, and five to eight zones are adequate for 2,000–6,000 ppm p-toluic acid based on TA initially in solution. However, those number of zones associated with p-toluic acid concentrations on TA are not the only number which can be successfully used for, as will be hereafter demonstrated, fiber-grade quality TA (i.e., not more than about 150 ppm p-toluic acid) can be recovered using 3–6 stirred crystallization zones when the p-toluic acid content on TA is 1,500 to 6,000 ppm. For said 1,500–6,000 ppm p-toluic acid content TA, it is preferred to use 3–6 zones of solvent flash evaporation. It is also preferred, from the standpoint of capital investment cost for commercial operation of the present inventive continuous process, to use 2–6 zones of flash solvent evaporation for initial p-toluic acid concentrations on TA in the range of 500–6,000 ppm by weight.

For the conduct of each of the 2–8, preferably 3–6 zones of flash solvent evaporation, each incremental amount of original water evaporated is not returned to any stage of the process. Selection of the operating temperature for each flash solvent evaporation in the series of 2–8, preferably 3–6, stirred crystallization zones can be judiciously made from a plot of TA saturation concentration against temperature so that the temperature profile of the entire process reasonably follows said plot. The illustrative examples hereinafter presented will provide a number of such temperature profiles which can be followed to obtain the same results indicated or which can serve as guidance for selecting different temperature profiles for operating with solutions having concentrations of p-toluic acid differing from those illustrated but within the range of 500–6,000 ppm by weight on TA.

The present inventive continuous TA crystallization process, surprisingly successful in its application of the concept of flash solvent evaporation, also is based on the discovery that contamination of final TA product by rejection of p-toluic acid from solution not saturated therewith is, however, a temperature-dependent phenomenon rather than a cooling-rate dependent phenomenon. The application of such discovery of temperature-dependent phenomenon to the present inventive process does not mean that selection of a temperature profile for operation of such process is limited by a critical single final crystallization temperature above which no p-toluic acid will be rejected from a solution not saturated with p-toluic acid and thus limit the flexability of operation of the present inventive continuous process. As demonstrated later in an illustrative example, some p-toluic acid is rejected from solution with each incremental amount of TA crystallized. But even this does not impose a substantial limitation on the flexability of the present inventive process.

Rather substantial flexability of operation of the present inventive process is possible with respect to the initial aqueous solution feed contents of not only dissolved TA and its p-toluic acid content within the range of 500–6,000 ppm by weight, but also with respect to selection of a number of stirred crystallization zones and even the final quality of TA product. The temperature-dependent p-toluic acid rejection becomes of importance after a temperature in the range of 360°–320° F. has been reached. The increments of originally dissolved TA crystallized in each such zone can be substantial until said 360°–320° F. temperature is reached and thereafter each crystallized increment of originally dissolved TA should be decreasingly smaller. But each of such smaller increment is not restricted to a critically limiting single fraction of originally dissolved TA. Even with respect to such temperature-dependent phenomenon and need to diminish the increments of TA crystallized below said 360°–320° F. temperature range, which range indicates flexibility rather than inflexibility of operation, the illustrative modes of operation of the present inventive process will provide guidance for selecting the number of crystallization zones as well as the increment of TA to be crystallized in each such zone operated below said temperature range.

In general, the key factor to selecting the temperature profile for the crystallization zones from 360°–320° F. and below involves the selection of each zone temperature so that each increment of TA crystallized in each stage is progressively smaller than the increment of the preceding zone. This will not only minimize the proportion of TA crystallized below the 340°–320° F. range but also minimize p-toluic acid contamination.

The following three operations demonstrate that, with respect to the use of flash evaporation of solvent and attendant substantially instantaneous precipitation of TA crystals, the concept of control of final temperature of crystallization and product separation at 250°–300° C. or the concept of TA rate controlled crystallization are not applicable with respect to limiting p-toluic acid contamination of recovered TA product.

COMPARATIVE EXAMPLE 1

An aqueous solution containing 20 weight percent TA (25 pounds TA per 100 pounds of water) and 2,500 ppm p-toluic acid based on TA at a temperature of 515° F. and 800 pounds per square inch absolute (psia) pressure is used as feed into a stirred crystallization zone operated at a temperature of 300° F. and 67 psia. Such solution is charged continuously to said zone through a flow control valve immediately adjacent to the inlet port of the crystallizer. The steam generated by the flash evaporation of water from 515° to 300° F. is withdrawn from the crystallizer, condensed and discarded. The resulting suspension of TA crystals is centrifuged at a temperature of 300° F. and a pressure of 67 psia. The recovered solid crystalline TA is dried. The dry TA product obtained by such operation will be found to contain about 1,200 ppm by weight of p-toluic acid.

COMPARATIVE EXAMPLE 2

The above process is repeated except the p-toluic acid content of dissolved TA is 500 ppm by weight. The recovered dry TA product produced by such operation will be found to contain about 250 ppm of p-toluic acid by weight.

COMPARATIVE EXAMPLE 3

TA containing 2,500 ppm of p-toluic acid is dissolved in water at 530° F. and 858 psia to provide a solution containing 25 pounds TA for each 100 pounds of water. Four stirred crystallization zones each are connected in series for continuous flow operation. A temperature profile is selected so that substantially equal increments of originally dissolved TA are crystallized in each such zone. The respective operating temperatures and pressures are: 502° F. and 674.7 psia; 485° F. and 580.7 psia; 457° F. and 447.2 psia; and 300° F. and 67 psia. The solution is charged at the rate to provide 100 pounds TA per hour to the first zone. The amounts of water vapor generated from each zone in pounds per hour are respectively: 31.48; 19.36; 23.1; and 70.73. The respective amounts of TA crystallized on an hourly basis are: 28.37; 25.03; 23.17; and 22.85. The suspension from the fourth zone flows at an hourly rate of 355.6 pounds per hour and contains 99.6 pounds suspended solids and 256.1 pounds aqueous mother liquor. Said suspension is centifuged at a temperature of 300° F. and 67 psia. The recovered and dried TA produced by such operation will be found to contain about 420 ppm of p-toluic acid.

The above operation had an adequate number of crystallization zones, as later illustrative Examples 1 and 3 demonstrate, a final crystallization and separation temperature meeting the prior art requirements and a temperature profile logically acceptable from the prior art rate dependent phenomenon. But the final TA product is of unacceptable quality (well above the maximum of 150 ppm of p-toluic acid) because the TA increment crystallized at 300° F. was too large.

The foregoing three operations are, of course, outside the scope of the present invention.

The aqueous solution fed to the first of the 2–8, preferably 3–6, flash solvent evaporation zones of the present inventive process wherein attendant TA crystallization is substantially instantaneous can be solutions substantially saturated with TA at temperatures in the range of 400° to 550° F. which correspond to TA saturation concentrations on a weight basis of 2 to 50 parts TA per 100 parts of water. The p-toluic acid content of such dissolved TA is in the range of 500–6,000 ppm also on a weight basis. For material handling economics, it is preferred to use as feed solutions to the first zone those solutions which contain 10–30 parts TA per 100 parts of water. The corresponding TA saturation temperatures are in the range of 468° to 522° F. However, to prevent premature TA crystallization during transfer to said first zone (i.e., from the catalytic hydrogenation purification of first stage), it is preferred that such feed solutions containing 10–30 parts TA per 100 parts water be at a temperature of at least about 10° to 20° F. (5° to 10° C.) above the corresponding saturation temperatures and preferably at a temperature in the range of 482° to 536° F.

The present inventive continuous TA crystallization process has another feature unique in view of prior art teachings. Said unique feature is that the crystalline TA magma produced can be readily recovered by continuous centrifuging in spite of prior teachings that instantaneous crystallization of TA from solution produces a crystalline magma containing sufficient small crystals to plug the centrifuge cake and make solid-liquid separation by continuous centrifuging not feasible as a commercial operation.

The following examples illustrate useful modes of conduct for the present inventive process using feeds of different TA concentrations, dissolved TA of different p-toluic acid content within the range of 500–6,000 ppm, different number of solvent flash evaporation - TA crystallization stirred zones within the 2–8 zone range, and different temperatures for final TA crystallization even down to 212° F. In all the illustrative examples the feed solution is charged to the first of such solvent flash evaporation, stirred TA crystallization zones at a flow rate to provide thereto of 100 pounds TA per hour. The TA is recovered by continuous centrifuging, is washed with fresh water to remove adhering mother liquor and is then dried. Water washing of wet TA centrifuge product reduces the p-toluic acid content of such TA product only by the amount of p-toluic acid remaining as solute in the adhering small amount of mother liquor.

In each of the following three examples, the feed solutions to the first crystallization zone contain 20 weight percent TA (25 pounds per 100 pounds of water) of 2,500 ppm p-toluic acid content. Such feed solution is at a temperature of 515° F. (5° F. above saturation temperature) and a pressure of 800 psia to keep the water in the liquid phase. The number of flash solvent evaporation stages are 3, 5 and 6.

EXAMPLES 1 to 3

For the 3, 5 and 6 multi-zone continuous flash evaporation, crystallizations, the above-described feed solution is continuously charged to the first stirred zone. The magma (crystals plus solution) produced in each stirred zone is charged sequentially to each of the following stirred zones. The magma produced in the last zone is charged continuously to the centrifuge. In all three operations the last stirred zone and the centrifuge are operated at the temperature of 300° F. and pressure of 67 psia. The temperature (T, °F.) and pressure (P, psia) for each crystallization step and the centrifuge for conduct of the 3, 5 and 6 series connected stirred zone operations are indicated in TABLE I. The p-toluic acid content of dried centrifuge cake (ppm on TA) from such processes will not exceed the values shown in TABLE I.

TABLE I

CONTINUOUS FLASH SOLVENT EVAPORATION, TA CRYSTALLIZATION

Aqueous Feed Solution: 20 wt. % TA with 2500 ppm p-Toluic Acid at 515°F. and 800 psia

| Stirred Zone | Example 1 | Example 2 | Example 3 |
|---|---|---|---|
| First: T, °F. | 420 | 460 | 460 |
| P, psia | 300 | 460 | 460 |
| Second: T, °F. | 350 | 410 | 420 |
| P, psia | 130 | 270 | 300 |
| Third: T, °F. | 300 | 370 | 390 |
| P, psia | 67 | 170 | 215 |
| Fourth: T, °F. | Not | 330 | 350 |
| P, psia | Used | 100 | 130 |
| Fifth: T, °F. | Not | 300 | 330 |
| P, psia | Used | 67 | 100 |
| Sixth: T, °F. | Not | Not | 300 |
| P, psia | Used | Used | 67 |
| Centrifuge: | | | |
| T, °F. | 300 | 300 | 300 |
| P, psia | 67 | 67 | 67 |
| Cake p-Toluic Acid | 85 ppm | 50 ppm | 44 ppm |

EXAMPLES 4-6

The process of Examples 1-3 is repeated using the feed solutions, number of stirred zones, temperatures and pressures shown in TABLE II below.

TABLE II

CONTINUOUS FLASH SOLVENT EVAPORATION, TA CRYSTALLIZATION

| Feed Solution: | Example 4 | Example 5 | Example 6 |
|---|---|---|---|
| TA, wt.% | 20 | 20 | 20 |
| p-Toluic acid ppm | 2,500 | 2,500 | 2,000 |
| T, °F. | 515 | 530 | 515 |
| P, psia | 800 | 857 | 800 |
| Stirred Zone | | | |
| First: T, °F. | 460 | 443 | 400 |
| P, psia | 460 | 389.5 | 220 |
| Second: T, °F. | 380 | 371 | 300 |
| P, psia | 195 | 175 | 67 |
| Third: T, °F. | 330 | 300 | Not |
| P, psia | 100 | 67 | Used |
| Fourth: T, °F. | 290 | Not | Not |
| P, psia | | Used | Used |
| Fifth: T, °F. | 260 | Not | Not |
| P, psia | | Used | Used |
| Sixth: T, °F. | 212 | Not | Not |
| P, psia | 14.7 | Used | Used |
| Centrifuge: | | | |
| T, °F. | 212 | 300 | 300 |
| P, psia | 14.7 | 67 | 67 |
| Cake p-Toluic Acid | 150 | 87 | 150 |

It will be noted that in Example 5, the temperature differences between feed and first zone and between subsequent zones are substantially equal. Such operation still produces decreasing incremental amounts of crystallized TA which are 83.4; 13.7; and 2.45% of initially dissolved TA, respectively, in zones 1, 2 and 3.

In Example 7, which follows, the feed solution contains 20 weight percent TA of 1610 ppm p-toluic acid content and has a temperature of 530° F. and a pressure of 859 psia to maintain water in the liquid phase. Said solution is continuously fed at a rate to provide 100 pounds TA per hour to the first of six flash solvent evaporation stirred TA crystallization zones in series operated as before described. In this example, the conditions of operation for each of the six zones, the percent of original TA crystallized in each zone on an hourly basis, the temperature and pressure of solid-liquid separation in the centrifuge, the percent of original TA recovered, and the p-toluic acid content in ppm of recovered and dried (unwashed) TA product are listed in TABLE III. This example differs in mode of conduct from all the other examples in that substantially equal amounts of TA are cryatallized in zones 1 and 2 and the total TA crystallized thereby represents 93 weight percent of the TA in the feed solution.

TABLE III

Example 7
Feed Solution: 18 wt.% TA of 1610 ppm Content p-Toluic Acid
Temperature 530° F.
Pressure 860 psia

| Stirred Zone | Temperature °F. | Pressure psia | %TA Crystallized |
|---|---|---|---|
| 1 | 485 | 580.7 | 45.83 |
| 2 | 400 | 246.2 | 47.20 |
| 3 | 330 | 102.9 | 5.63 |
| 4 | 275 | 45.4 | 0.97 |
| 5 | 250 | 29.8 | 0.16 |
| 6 | 215 | 15.6 | 0.12 |
| Centrifuge | 215 | 15.6 | 99.91 | p-toluic acid content of recovered TA product: 102 ppm

The dry TA product resulting from operation according to Example 7 is unique with respect to its particle size distribution characteristics. Such product has a rather broad particle size distribution over the range of 0 to 450 microns, a large proportion of the particles are of about 250 microns in size and there are two particle size peaks in the particle size distribution. Such particle size distribution is characteristic of a bi-modal distribution and not of a normal distribution of particles from the ordinary crystallization. Thus, the technique of Example 7 provides a route to a unique crystalline fiber-grade quality TA. Such unique bi-modal crystalline products can be obtained by crystallizing 75-95% of total TA in substantially equal proportions in the first two of 3-6 series connected stirred zones according to the present process.

The following examples comprise illustrative Examples 8 and 9 and comparative Example 4 which is similar to Example 8 but omits its crystallization zone operated at 330° F. and crystallizes at 275° F. the proportion of original TA equal to the sum of such proportions crystallized in Example 8 in its 330° F. and 275° F. zones. These three examples illustrate the proper and improper crystallization of diminishing proportions of originally dissolved TA from the 360°–320° F. range to lower temperatures with respect to p-toluic acid contamination of final TA product.

The feed solutions to each of illustrative Examples 8 and 9 and comparative Example 4 are at a temperature of 530° F. and pressure of 859 psia to maintain water in the liquid phase and contain 18 weight percent of TA having 2,000 ppm content of p-toluic acid. Such solutions are fed to the first of the series connected crystallization zones at a rate to provide 100 pounds TA per hour to the first zone. The temperature and pressure conditions of operation of the zones and centrifuge, the weight percent proportion of TA crystallized in each zone and the total percent TA crystallized, and the p-toluic acid content of recovered TA product are all given in TABLE IV.

TABLE IV

CONTINUOUS SOLVENT EVAPORATION, TA CRYSTALLIZATION

| Feed Solution | Example 8 | Comparative Example 4 | Example 9 |
|---|---|---|---|
| TA, wt.% | 18 | 18 | 18 |
| T, °F. | 530 | 530 | 530 |
| P, psia | 859 | 859 | 859 |
| Stirred Zone | | | |
| First: T, °F. | 485 | 485 | 400 |
| P, psia | 580 | 580 | 246.2 |
| Crystallized TA, wt.% | 45.83 | 45.83 | 93.03 |
| Second: T, °F. | 400 | 400 | 330 |
| P, psia | 246.2 | 246.2 | 102.9 |
| Crystallized TA, wt.% | 47.20 | 47.20 | 5.63 |
| Third: T, °F. | 330 | 275 | 275 |
| P, psia | 102.9 | 45.4 | 45.4 |
| Crystallized TA, wt.% | 5.63 | 6.61 | 0.97 |
| Fourth: T, °F. | 275 | 250 | 250 |
| P, psia | 45.4 | 29.8 | 29.8 |
| Crystallized TA, wt.% | 0.97 | 0.16 | 0.16 |
| Fifth: T, °F. | 250 | 212 | 212 |
| P, psia | 29.8 | 14.7 | 14.7 |
| Crystallized TA, wt.% | 0.16 | 0.12 | 0.12 |
| Sixth: T, °F. | 212 | Not Used | Not Used |
| P, psia | 14.7 | | |
| Crystallized TA, wt.% | 0.12 | | |
| Centrifuge: | | | |
| T, °F. | 212 | 212 | 212 |
| P, psia | 14.7 | 14.7 | 14.7 |
| Recovered Ta, wt.% | 99.91 | 99.91 | 99.91 |
| Cake p-Toluic Acid | 133 ppm | 274 ppm | 153 ppm |

With respect to the TA product from Example 9, a simple wash of the centrifuge cake with fresh water at a temperature of 200°–205° F. will lower the p-toluic acid content of the washed and dried product to less than 150 ppm. However, such washing of the product of Comparative Example 4 will not provide a washed, dried product of less than 150 ppm content of a p-toluic acid. Sampling and analyzing the TA product after the third crystallization zone of Comparative Example 4 will show that TA product to have over 200 ppm p-toluic acid. Hence, operation according to Comparative Example 4 is to be avoided.

In the following Examples 10, 11 and 12, the feed solutions contain 20 weight percent TA of varying p-toluic acid content, have the same temperature of 530° F. and pressure of 857 psia to maintain water in the liquid phase, and are fed at a rate to provide 100 pounds TA per hour to the first zone. The pertinent data for these crystallizations are given in TABLE V.

TABLE V

CONTINUOUS SOLVENT EVAPORATION, TA CRYSTALLIZATION

| Feed Solution | Example 10 | Example 11 | Example 12 |
|---|---|---|---|
| TA, Wt.% | 20 | 20 | 20 |
| P-Toluic Acid Content | 4,000 | 6,000 | 600 |
| T, °F. | 530 | 530 | 530 |
| P, psia | 857 | 857 | 857 |
| Stirred Zone | | | |
| First: T, °F. | 440 | 440 | 420 |
| P, psia | 378 | 378 | 307 |
| Crystallized TA, wt.% | 84.45 | 84.45 | 90.36 |
| Second: T, °F. | 380 | 380 | 340 |
| P, psia | 195 | 195 | 118 |
| Crystallized TA, wt.% | 11.81 | 11.81 | 8.18 |
| Third: T, °F. | 340 | 340 | 270 |
| P, psia | 118 | 118 | 42 |
| Crystallized TA, wt.% | 2.28 | 2.28 | 1.18 |
| Fourth: T, °F. | 310 | 310 | 212 |
| P, psia | 78 | 78 | 14.7 |
| Crystallized TA, wt.% | 0.74 | 0.74 | 0.21 |
| Fifth: T, °F. | 285 | 285 | Not Used |
| P, psia | 53 | 53 | |
| Crystallized TA, wt.% | 0.32 | 0.32 | |
| Centrifuge: | | | |
| T, °F. | 285 | 285 | 212 |
| P, psia | 53 | 53 | 14.7 |
| Recovered TA, wt.% | 99.6 | 99.6 | 99.93 |
| Cake p-toluic acid | 98.7 | 148.1 | 62.9 |

EXAMPLE 13

This illustration of the present inventive continuous TA crystallization charges the aqueous solution to the first crystallization zone of eight stirred zones at a rate to provide 100 pounds TA per hour. The feed solution is at a temperature of 530° F. and a pressure of 858 psia to maintain water as liquid phase and contains 20 weight percent of TA with a 2,500 ppm content of p-toluic acid. A total of 169.6 pounds of water are flash evaporated. The conditions of operation of each stirred zone, the cumulative percent TA crystallized and the p-toluic acid content thereof are given in the following table.

TABLE VI

| Stirred Zone | Temperature °F. | Pressure psia | Cumulative % Crystallized TA | p-Toluic Acid Content |
|---|---|---|---|---|
| 1 | 460 | 460 | 74.79 | 7 |
| 2 | 410 | 275 | 92.40 | 13 |
| 3 | 360 | 153 | 97.67 | 26 |
| 4 | 320 | 90 | 99.09 | 41 |
| 5 | 280 | 49 | 99.64 | 65 |
| 6 | 250 | 30 | 99.82 | 90 |
| 7 | 230 | 21 | 99.89 | 109 |
| 8 | 212 | 14.7 | 99.93 | 131 |
| Centrifuge | 212 | 14.7 | 99.93 | 131 |

The final TA product recovered meets the p-toluic acid maximum content of not exceeding 150 ppm. However, TA product could have been recovered from the magma resulting from the first six crystallization stages without any substantial yield loss with a p-toluic acid content of about 89 ppm which is comparable to the 87 ppm p-toluic acid content of TA product from Example 5. It will also be noted that the TA product of Example 13, because of the temperature profile for TA increments crystallized below the 360°–320° F. range as compared against the same profile of Example 4, resulted in a higher quality TA (131 v. 150 ppm p- toluic acid) than recovered from the process of Example 4.

What is claimed is:

1. For the recovery of crystalline terephthalic acid product having a maximum p-toluic acid content not exceeding 150 ppm from a liquid aqueous solution substantially saturated with terephthalic acid containing 500–6,000 ppm of p-toluic acid at a temperature in the range of 400° to 550° F., the improved process comprising continuously charging such aqueous solution to the first of two or more series connected flash solvent evaporation and stirred crystallization zones each operated at a successively lower temperature wherein at least the zones operated at a temperature within and below the range of 360°–320° F. crystallize decreasing proportions of originally dissolved terephthalic acid, the flash evaporated solvent is removed from each zone and the temperature of recovery of terephthalic acid product is the same as the temperature of the last zone.

2. The process of claim 1 wherein the number of series connected zones is in the range of from 2 to 8.

3. The process of claim 1 wherein the number of series connected zones is in the range of from 3 to 6 for initial liquid aqueous solutions of terephthalic acid of 1,500–6,000 ppm p-toluic acid content.

4. The process of claim 3 wherein a total of 75–95% of originally dissolved terephthalic acid is crystallized in substantially equal proportions in the first two zones at a temperature above the range of 360°–320° F. and thereafter the remaining 5–25% proportion of originally dissolved terephthalic acid is crystallized in decreasing incremental proportions.

5. The process of claim 3 wherein the incremental proportions of terephthalic acid crystallized decrease from the first to the last zone.

6. The process of claim 5 wherein a substantially equal temperature difference between the temperature of the feed and first zone and between the temperatures of each of the subsequent zones is maintained.

7. The process of claim 5 wherein the number of zones is in the range of from 2 to 6 and the temperature of the last zone is 300° F.

8. The process of claim 5 wherein the number of zones is in the range of from 4 to 8 and the temperature of the last zone is in the range of 212° to 285° F.

* * * * *

UNITED STATES PATENT OFFICE
CERTIFICATE OF CORRECTION

PATENT NO. : 3,931,305
DATED : January 6, 1976
INVENTOR(S) : Jay A. Fisher

It is certified that error appears in the above-identified patent and that said Letters Patent are hereby corrected as shown below:

| Column | Line | |
|---|---|---|
| 2 | 7 | "300°F. terephthalic" should be --300°F., terephthalic-- |
| 6 | 15 | "of" should be --to-- |

Signed and Sealed this twenty-fifth Day of May 1976

[SEAL]

Attest:

RUTH C. MASON
Attesting Officer

C. MARSHALL DANN
Commissioner of Patents and Trademarks